United States Patent
Hamilton et al.

(10) Patent No.: US 6,325,810 B1
(45) Date of Patent: Dec. 4, 2001

(54) FOAM BUTTRESS FOR STAPLING APPARATUS

(75) Inventors: Leslie Hamilton, Ringoes; Rao S. Bezwada, Whitehouse Station; Mark B. Roller, North Brunswick; Murty N. Vyakarnam, Edison; David A. Dalessandro, Fanwood; Joel S. Rosenblatt, Watchung; Ram L. Kataria, Hamilton Square; Lowell G. Saferstein, West Orange, all of NJ (US); James F. Martin, Lebanon, OH (US)

(73) Assignee: Ethicon, Inc., Skillman, NJ (US)

( * ) Notice: Subject to any disclaimer, the term of this patent is extended or adjusted under 35 U.S.C. 154(b) by 0 days.

(21) Appl. No.: 09/345,093

(22) Filed: Jun. 30, 1999

(51) Int. Cl.[7] .................................................... A61B 17/04
(52) U.S. Cl. ........................................ 606/151; 227/175.1
(58) Field of Search .................................... 606/151, 153, 606/219; 227/19, 176.1

(56) References Cited

U.S. PATENT DOCUMENTS

| | | |
|---|---|---|
| 2,671,444 | 3/1954 | Pease, Jr. . |
| 3,054,406 | 9/1962 | Usher . |
| 3,079,606 | 3/1963 | Bobrov et al. . |
| 3,108,357 | 10/1963 | Liebig . |
| 3,122,140 | 2/1964 | Crowe, Jr. . |
| 3,124,136 | 3/1964 | Usher . |
| 3,272,204 | 9/1966 | Artandi et al. . |
| 3,276,448 | 10/1966 | Kronenthal . |
| 3,284,557 | 11/1966 | Polansky . |
| 3,463,158 | 8/1969 | Schmitt et al. . |
| 3,490,675 | 1/1970 | Green et al. . |
| 3,620,218 | 11/1971 | Schmitt et al. . |
| 3,636,956 | 1/1972 | Schneider . |
| 3,688,317 | 9/1972 | Kurtz . |
| 3,739,773 | 6/1973 | Schmitt et al. . |
| 3,875,937 | 4/1975 | Schmitt et al. . |
| 3,937,223 | 2/1976 | Roth . |
| 4,128,612 | 12/1978 | Roth . |
| 4,132,839 | 1/1979 | Marans et al. . |

(List continued on next page.)

FOREIGN PATENT DOCUMENTS

| | | | |
|---|---|---|---|
| 0334046 | 2/1989 | (EP) . | |
| 0325195 | 7/1989 | (EP) . | |
| 0 594 148 A1 | 4/1994 | (EP) | ............................... A61L/31/00 |
| 0 922 435 A1 | 6/1999 | (EP) | ............................... A61B/17/03 |

OTHER PUBLICATIONS

"Clinical Applications of Bioabsorbable PGA Sheets for Suture Reinforcement and Use as Artificial Pleura"; Tatsuo Nakamura et al.; Japan Lung Surgery Journal 40:10.8(1826)1992.

"Reinforced Staple Line in Severely Emphysematous Lungs"; F. M. Juettner, MD et al.; Graz. Austria Journal of Thorac and Cardiovasc Surgery 1989; 97:362–3.

"Median Sternotomy for Bilateral Resecton of Emphysematous Bullae"; Oriane Lima, MD et al.; Ontario, Canada Journal of Thorac and Cardiovasc Surgery 1981; 82:892–897.

"The Current Status of Surgery for Bullous Emphysema", J. E. Connolly, MD et al.; Irvine, California Journal of Thorac and Cardiovasc Surgery 1989;97:351–61.

"Prevention of Postoperative Pericardial Adhesions by Closure of the Pericardium with Absorbable Polymer Patches"; Malm et al.,; The Journal of Thorac and Cardiovascular Surgery, vol. 104, No. 3, pp. 600–607; Sep. 1992.

*Primary Examiner*—Gary Jackson (57) ABSTRACT

An apparatus for achieving hemostasis and pneumostasis along a staple line by utilizing a compliant bioabsorbable foam buttress which may be attached to one jaw of a surgical stapling apparatus by a biocompatible releasable adhesive.

33 Claims, 5 Drawing Sheets

U.S. PATENT DOCUMENTS

| | | |
|---|---|---|
| 4,164,046 | 8/1979 | Cooley . |
| 4,186,448 | 2/1980 | Brekke . |
| 4,215,686 | 8/1980 | Gregory et al. . |
| 4,347,847 | 9/1982 | Usher . |
| 4,354,628 | 10/1982 | Green . |
| 4,397,311 | 8/1983 | Kanshin et al. . |
| 4,429,695 | 2/1984 | Green . |
| 4,452,245 | 6/1984 | Usher . |
| 4,508,253 | 4/1985 | Green . |
| 4,520,817 | 6/1985 | Green . |
| 4,520,821 | 6/1985 | Schmidt et al. . |
| 4,548,202 | 10/1985 | Duncan . |
| 4,568,009 | 2/1986 | Green . |
| 4,608,981 | 9/1986 | Rothfuss et al. . |
| 4,626,253 | 12/1986 | Broadmax, Jr. . |
| 4,633,861 | 1/1987 | Chow et al. . |
| 4,633,873 | 1/1987 | Dumican et al. . |
| 4,633,874 | 1/1987 | Chow et al. . |
| 4,652,264 | 3/1987 | Dumican . |
| 4,655,221 | 4/1987 | Devereux . |
| 4,681,588 | 7/1987 | Ketharanathan . |
| 4,702,917 | 10/1987 | Schindler . |
| 4,728,020 | 3/1988 | Green et al. . |
| 4,784,137 | 11/1988 | Kulik et al. . |
| 4,832,686 | 5/1989 | Anderson . |
| 4,838,884 | 6/1989 | Dumican et al. . |
| 4,840,626 | 6/1989 | Linsky et al. . |
| 4,865,031 | 9/1989 | O'Keeffe . |
| 4,892,244 | 1/1990 | Fox et al. . |
| 4,905,692 | 3/1990 | More . |
| 4,930,674 | 6/1990 | Barak . |
| 4,932,960 | 6/1990 | Green et al. . |
| 4,955,959 | 9/1990 | Tompkins et al. . |
| 4,960,866 | 10/1990 | Bendix et al. . |
| 4,983,745 | 1/1991 | Muller et al. . |
| 5,002,551 | 3/1991 | Linsky et al. . |
| 5,011,493 | 4/1991 | Belykh et al. . |
| 5,014,899 | 5/1991 | Presty et al. . |
| 5,040,715 | 8/1991 | Green et al. . |
| 5,042,707 | 8/1991 | Taheri . |
| 5,061,281 | 10/1991 | Mares et al. . |
| 5,066,772 | 11/1991 | Tang et al. . |
| 5,079,075 | 1/1992 | Yamasaki et al. . |
| 5,102,983 | 4/1992 | Kennedy . |
| 5,141,144 | 8/1992 | Foslien et al. . |
| 5,156,614 | 10/1992 | Green et al. . |
| 5,156,797 | 10/1992 | Yamasaki et al. . |
| 5,176,692 | 1/1993 | Wilk et al. . |
| 5,203,864 | 4/1993 | Phillips . |
| 5,263,629 | 11/1993 | Trumbull et al. . |
| 5,346,115 | 9/1994 | Perouse et al. . |
| 5,397,324 | 3/1995 | Caroll et al. . |
| 5,433,721 | 7/1995 | Hooven et al. . |
| 5,441,193 | 8/1995 | Gravener . |
| 5,503,638 | 4/1996 | Cooper et al. . |
| 5,542,594 | 8/1996 | McKean et al. . |
| 5,702,409 | 12/1997 | Rayburn et al. . |
| 5,752,965 | 5/1998 | Francis et al. . |
| 5,766,188 | 6/1998 | Igaki . |
| 5,814,057 | 9/1998 | Oi et al. . |
| 5,964,774 | 10/1999 | McKean et al. . |

FOAM BUTTRESS FOR STAPLING APPARATUS

FIELD OF THE INVENTION

This invention relates to an apparatus for approximating tissue, more specifically it relates to a stapling apparatus that applies a biocompatible surgical foam buttress to body tissue.

BACKGROUND OF THE INVENTION

During surgical procedures it is necessary to approximate tissue organ with surgical staples. Surgeons often use linear cutter stapling devices to suture body organs and tissues such as lung, esophagus, stomach, duodenum and other body organs. Such devices apply a plurality of laterally spaced rows of staples on opposite sides of a tissue cut.

Examples of such surgical staplers are disclosed in U.S. Pat. Nos. 4,633,861 and 4,892,244, the disclosures of which are incorporated herein by reference. The surgical stapler includes a pair of cooperating elongated jaw members. One of the jaws members includes a staple cartridge with at least two laterally spaced rows of staples and the other jaw member includes an anvil with staple closing depressions in alignment with the rows of staples in the cartridge. A pusher block is directed longitudinally along the jaws to sequentially eject staples from the cartridges in a manner that closes the staples against the anvil to form laterally spaced lines of staples through tissues that is gripped between the jaws. A knife is associated with the pusher block so as to move forward along the jaws to cut the tissue along the line between the previously formed staple rows.

When operating on tissue it is desirable to close open blood vessels (hemostasis) along the cut line. And in procedures that involve approximating lung tissue it is necessary to seal the lung to avoid air leakage (pneumostasis). U.S. Pat. No. 5,263,629 discloses a method and apparatus for achieving hemostsis along a staple line by utilizing a pledget material positioned adjacent to at least one surface of the tissue. The line of staples is formed so as to extend through the tissue and the absorbable pledget material. The pledget material is selected so as to substantially uniformly distribute pressure along the staple line and thereby cause substantial hemostasis along the tissue cut. Preferred materials for these pledgets are sterile absorbable tightly woven fabrics. The pledgets may be secured to the stapler by spaced apart ultrasonic welds or spaced apart adhesive bonds.

The present invention provides an improved surgical stapling apparatus wherein the pledget material or buttress is an soft, compliant, bioabsorbable, foam material that is easy to cut and provides better sealing for hemostasis and pneumostasis which maybe releasably attached to the stapler by a low melting or liquid bioabsorbable polymer.

DETAILED DESCRIPTION OF THE INVENTION

Figure 1:
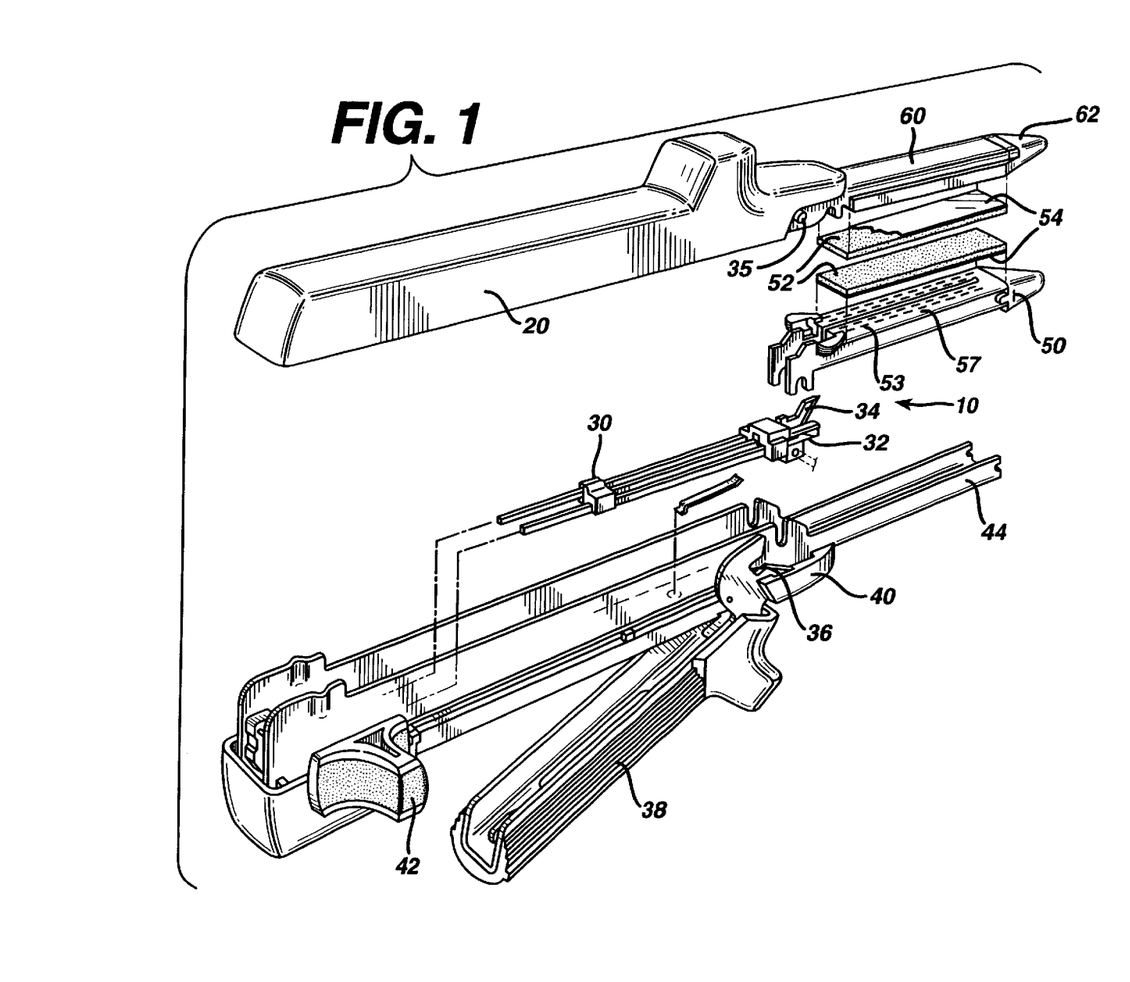
FIG. 1 is an exploded view in perspective of a surgical stapler device incorporating the biocompatible foam attached with a low-melting or liquid polymer.

Referring to FIG. 1, there is shown a typical surgical stapler 10 generally of the type disclosed in U.S. Pat. Nos. 4,633,861 and 4,892,244, the disclosure of which patents are incorporated herein by reference for a more complete discussion of certain structure details of the device. Surgical stapler 10 includes an upper jaw 20, a firing means 30, a lower jaw 40 and a staple cartridge 50 that is received within the lower jaw 40.

The firing means 30 includes a pusher block and firing wedge assembly 32 and a knife 34 located therebetween. The firing wedges are directed through longitudinal slots located in staple cartridge 50. Cartridge 50 is releasably received within a lower jaw channel 44. A firing knob 42 activates the firing means 30 to move the firing wedges 32 through the staple cartridge 50. As the firing wedges 32 pass longitudinally through the cartridge they contact staple drivers (not shown), which in turn eject the staples 51 through openings 53 in the staple cartridge 50.

Figure 2:
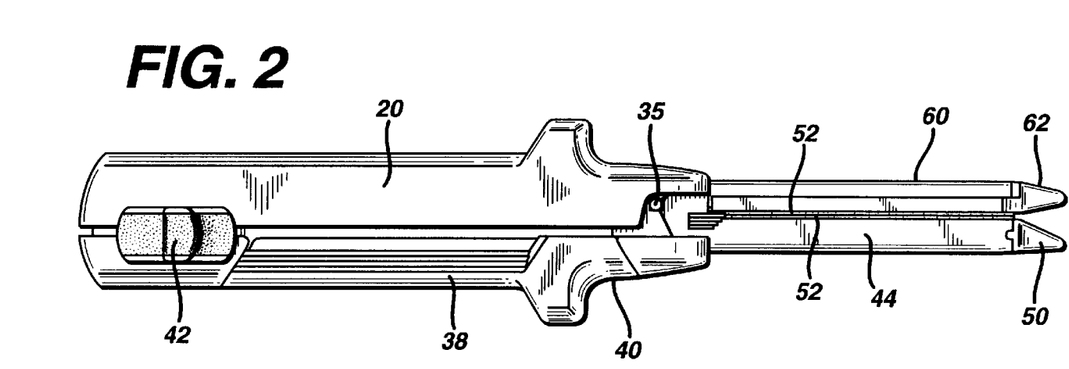
FIG. 2 is a side elevational view of the stapler device shown in FIG. 1 with its jaws in a clamping position.

Upper jaw 20 is pivotally connected to lower jaw 40 through a latch pin 35 that is received in a slot 36 associated with a latch member 38 to latch the jaw members together at an intermediate position along the length thereof. Movement of latch member 38 between its latched position, as shown in FIG. 2, and its unlatched position, as shown in FIG. 1, causes the jaws 20 and 40 to move toward and away from each other.

Figure 3:
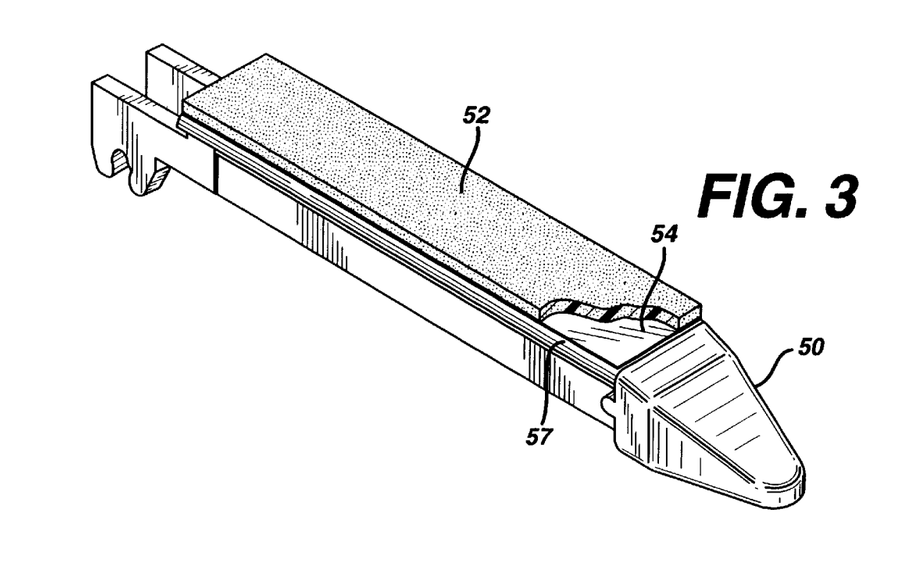
FIG. 3 is a perspective view of a staple cartridge that includes a foam material in accordance with the invention.

Referring to FIGS. 1 and 3 there is shown a preferred embodiment of a disposable staple cartridge 50 containing a plurality of surgical staples 51, of the type generally disclosed in U.S. Pat. Nos. 4,633,861 and 4,982,244. Cartridge 50 is preferably provided with two pairs of spaced apart parallel lines of staples. Cartridge 50 includes a strip of compliant bioabsorbable foam material 52 releasably attached thereto (by a low melting or liquid bioabsorbable polymer 54) in covering relationship with an upper surface 57 having openings 53 through which the staples are ejected in accordance with a preferred embodiment of the invention, the strip of foam is secured to the longitudinal edges of the staple cartridge of staple cartridge 50 by a continuous coating or a plurality of spaced apart releasable bonds provided by the low melting or liquid bioabsorbable polymer 54.

Referring to FIGS. 1 and 7–10, the front portion of upper jaw 20 includes an anvil section 60 that includes longitudinal rows of uniformly spaced staple-forming pockets 63. A disposable anvil tip 62 is releasably mounted at the front end of anvil section 60 and is received rearwardly there onto. Anvil tip 62 includes a leading tapered portion 64 to facilitate the insertion of the jaw member into hollow, tubular body organs or small openings in tissue sections. Anvil tip 62 includes a pair of spaced apart elongated inner side walls 66 that extend into anvil section 60 and a pair of spaced apart elongated outer side walls 68 that extend alongside anvil section 60. A foam material strip 52 may be releasably secured (adhesively or mechanically) to anvil tip 62 by a variety of means that permit the foam material strip to remain behind with the staples after the stapler has been removed from the staple site. In accordance with preferred embodiments of the invention, the strip of foam material is secured to the bottom surface of the side walls 68 by a continuous coating or a plurality of spaced apart releasable bonds formed by a releasable adhesive such as a low melting or liquid bioabsorbable polymer 54.

Figure 12:
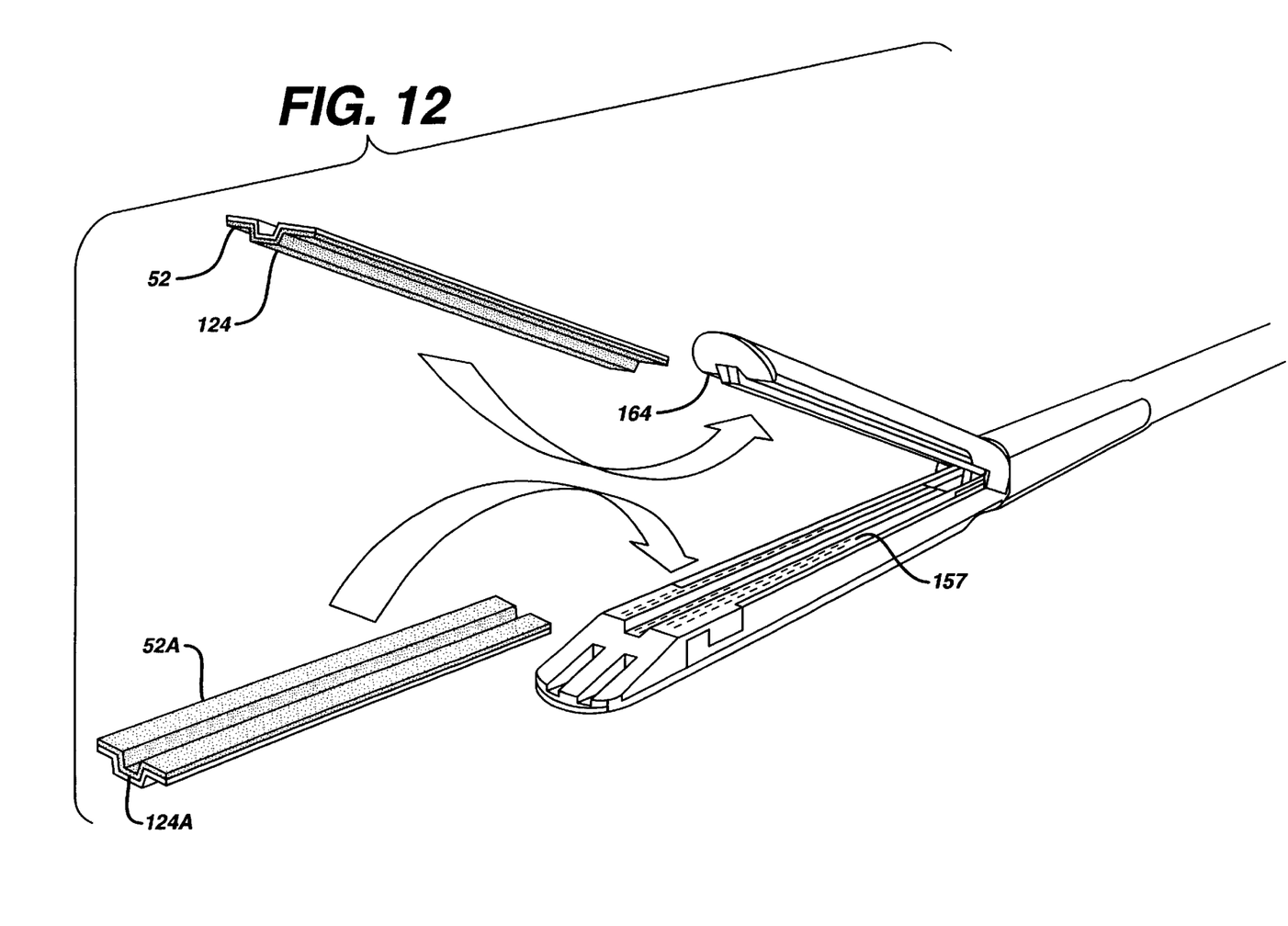
FIG. 12 is a perspective view of an alternative embodiment of the present invention in which the upper and optionally the lower jaws have contoured surfaces that are engaged by the foam material.

Alternatively, as illustrated in FIG. 12 the foam material 52, 52a may have features 124, 124a to engage the contoured surface of the anvil surface 164 or the contoured surface of cartridge 157.

In a further embodiment of the present invention, the foam material may be provided in a sleeve that fits over the jaws 20 and 40 of the stapler. Suitable designs for sleeves are described in U.S. Pat. Nos. 5,503,638; 5,702,409; and 5,766,188, which are hereby incorporated herein by reference. It is only necessary that the foam material be used on the portion of the sleeve that will remain in the patient for hemostasis or pneumostasis; the other portions of the sleeve may be made from other suitable materials.

In accordance with preferred embodiments of the invention, foam material strips 52 are preferably made from a compliant bioabsorbable foam material. The foam material uniformly distributes pressure along the staple line to cause substantial hemostasis or pneumostasis along the tissue cut. The foam material also provides a medium for the staples to hold on to in the case of thin or diseased tissue. The material also absorbs impact and reduces trauma.

Suitable foam materials for use as a buttress material need to be compliant and pliable so that the foam may distribute the compressive load and compensate for variations in tissue thickness, thereby acting as an effective gasket for hemostasis and pneumostasis.

Suitable foams for use in the present invention are prepared from biocompatible elastomeric polymers, preferably this polymer will also be bioabsorbable. Examples of suitable bioabsorbable elastomers are described in U.S. Pat. No. 5,468,253 hereby incorporated by reference. Preferably the bioabsorbable biocompatible elastomers are based on aliphatic polyester, including but not limited to those selected from the group consisting of elastomeric copolymers of ε-caprolactone and glycolide (preferably having a mole ratio of ε-caprolactone to glycolide of from about 35:65 to about 65:35, more preferably 45:55 to 35:65) elastomeric copolymers of ε-caprolactone and lactide, including L-lactide, D-lactide blends thereof or lactic acid copolymers (preferably having a mole ratio of ε-caprolactone to lactide of from about 35:65 to about 65:35 and more preferably 45:55 to 30:70 or from about 95:5 to about 85:15) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40) elastomeric copolymers of ε-caprolactone and p-dioxanone (preferably having a mole ratio of ε-caprolactone to p-dioxanone of from about 30:70 to about 70:30) elastomeric copolymers of p-dioxanone and trimethylene carbonate (preferably having a mole ratio of p-dioxanone to trimethylene carbonate of from about 30:70 to about 70:30), elastomeric copolymers of trimethylene carbonate and glycolide (preferably having a mole ratio of trimethylene carbonate to glycolide of from about 30:70 to about 70:30), elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. These elastomeric polymers will have an inherent viscosity of from about 1.2 dL/g to about 4 dL/g, preferably an inherent viscosity of from about 1.2 dL/g to about 2 dL/g and most preferably an inherent viscosity of from about 1.4 dL/g to about 2 dL/g as determined at 25° C. in a 0.1 gram per deciliter (g/dL) solution of polymer in hexafluoroisopropanol (HFIP).

Preferably, the elastomers will exhibit a high percent elongation and a low modulus, while possessing good tensile strength and good recovery characteristics. In the preferred embodiments of this invention, the elastomer from which the foams are formed will exhibit a percent elongation greater than about 200 preferably greater than about 500. It will also exhibit a modulus (Young's Modulus) of less than about 80,000 psi, preferably less than about 40,000 psi. There properties, which measure the degree of elasticity of the bioabsorbable elastomer, are achieved while maintaining a tensile strength greater than about 500 psi, preferably greater than about 1,000 psi, and a tear strength of greater than about 50 lbs/inch, preferably greater than about 80 lbs/inch.

These elastomer polymers may be foamed by lyophilization, supercritical solvent foaming (i.e., as described in EP 464,163 B1), gas injection extrusion, gas injection molding or casting with an extractable material (i.e., salts, sugar or any other means known to those skilled in the art). Currently it is preferred to prepare bioabsorbable, biocompatible elastomers by lyophilization. One suitable method for lyophilizing elastomeric polymers to form foams is described in Example 2. Pharmaceutically active compounds may be incorporated into the foam material to further treat the patient including are but not limited to antibiotics, antifungal agents, hemostatic agents, antiinflammatory agents, growth factors and the like.

Suitable bioabsorbable releasable adhesives, include aliphatic ester homopolymers and copolymers made from polymers of the formula:

wherein $R^{11}$ is selected from the group consisting of —$CR^{12}H$—, —$(CH_2)_3$—O—, —$CH_2$—$CH_2$—O—$CH_2$—, $CR^{12}H$—$CH_2$, —$(CH_2)_4$—, —$(CH_2)_z$—O— and —$(CH_2)_z$—$C(O)$—$CH_2$—; $R^{12}$ is hydrogen or methyl; z is an integer in the range of from 1 to 7; and y is an integer in the range of from about 10 to about 20,000; blends of a viscous PEG liquid and a low melting solid PEG (solid at room temperature that melts at less than about 60° C.); biocompatible monosaccharides, disaccharides and polysaccharides (such as pectin) that may be mixed with a plasticizer (such as glycerine) to form a tacky adhesive and biocompatible proteins (such as gelatin) that may mixed with a plasticizer (such as glycerine) to form a tacky adhesive.

Many nontoxic bioabsorbable aliphatic ester polymers that are semi-crystalline solids or tacky liquids at room temperature may be used as a releasable adhesive. The releasable adhesive of this invention are generally characterized as being flowable at body temperature (37° C.) and preferably will flow at room temperatures (25° C.). Most preferably these liquids will have a low yield point to avoid migration of the polymer. Examples of suitable tacky liquid copolymers are contained in U.S. patent application Ser. No. 08/746,180, filed Nov. 6, 1996 hereby incorporated by reference. Additionally, tacky microdispersions may also be used such as those described in U.S. Pat. No. 5,599,852, hereby incorporated by reference. In particular liquid copolymers composed of in the range of from about 65 mole percent to about 35 mole percent of $\epsilon$-caprolactone, trimethylene carbonate, ether lactone (which for the purpose of this invention is defined to be 1,4-dioxepan-2-one and 1,5-dioxepan-2-one) repeating units or combinations thereof with the remainder of the polymer being a plurality of second lactone repeating units are preferred. The second lactone repeating units will be selected from the group consisting of glycolic acid repeating units, lactic acid repeating units, 1,4-dioxanone repeating units, 6,6-dialkyl-1,4-dioxepan-2-one, combinations thereof and blends thereof. Additionally, $\epsilon$-caprolactone, trimethylene carbonate, or an ether lactone may be copolymerized to provide a liquid copolymer. Preferred polymers for use as particulate solids are bioabsorbable polymers including homopolymers of poly($\epsilon$-caprolactone), poly(p-dioxanone), or poly(trimethylene carbonate), copolymers of $\epsilon$-caprolactone and trimethylene carbonate, copolymers of $\epsilon$-caprolactone and a plurality of second lactone repeating units. The second lactone repeating units may be selected from the group consisting of glycolic acid repeating units, lactic acid repeating units, 1,4-dioxanone repeating units, 1,4-dioxepan-2-one repeating units, 1,5-dioxepan-2-one repeating units and combinations thereof. The copolymers of $\epsilon$-caprolactone will preferably be composed of from 99 mole percent to 70 mole percent $\epsilon$-caprolactone with the remainder of the polymer being a plurality of second lactone repeating units. The polymers may be linear, branched, or star branched; block copolymers or terpolymers; segmented block copolymers or terpolymers. These polymers will also be purified to substantially remove unreacted monomers that may cause an inflammatory reaction in tissue.

Preferred liquid copolymers for use as the releasable adhesive are composed of in the range of from about 65 mole percent to about 35 mole percent $\epsilon$-caprolactone or an ether lactone repeating unit with the remainder of the copolymer being trimethylene carbonate repeating units. Examples of suitable terpolymers are terpolymers selected from the group consisting of poly(glycolide-co-$\epsilon$-caprolactone-co-p-dioxanone) and poly(lactide-co-$\epsilon$caprolactone-co-p-dioxanone) wherein the mole percent of $\epsilon$-caprolactone repeating units is from about 35 to about 65 mole percent.

Preferred are terpolymers having in the range of from 40 to 60 mole percent of $\epsilon$-caprolactone repeating units. Examples of liquid copolymer for use as the releasable adhesive may be selected from the group consisting of poly($\epsilon$-caprolactone-co-trimethylene carbonate), poly(lactide-co-trimethylene carbonate), poly($\epsilon$-caprolactone-co-p-dioxanone), poly(trimethylene carbonate-co-p-dioxanone), poly($\epsilon$-caprolactone-co-lactide), poly(lactide-co-1,5-dioxepan-2-one), and poly(1,5-dioxepan-2-one-co-p-dioxanone), poly(lactide-co-1,4-dioxepan-2-one), and poly(1,4-dioxepan-2-one-co-p-dioxanone). The mole percent of $\epsilon$-caprolactone, trimethylene carbonate or ether lactone repeating units in these polymers should be in the range of from about 35 to about 65 mole percent and preferably in the range of from 40 to 60 mole percent. Most preferably these liquid polymers will be statistically random copolymers. These polymers will also be purified to substantially remove unreacted monomers that may cause an inflammatory reaction in tissue.

The polymers used as the releasable adhesive should have an inherent viscosity as determined in a 0.1 g/dL solution of hexafluoroisopropanol (HFIP) at 25° C. ranging from about 0.1 dL/g to about 0.8 dL/g, preferably from about 0.1 dL/g to about 0.6 dL/g, and most preferably from 0.15 dL/g to 0.25 dL/g for liquid polymers.

Additionally, blends of liquid and solid polyethylene glycols (PEG) may be used as releasable adhesives. The liquid PEG may have a molecular weight from about 200 to about 600. The solid PEG may have a molecular weight from about 3400 to about 10,000. Generally it is theorized, but in no way limits the scope of this invention, that the low molecular weight liquid PEG plasticizes the solid PEG to render the solid PEG tacky. Consequently the majority of the composition should be the solid PEG and preferably between about 50 and about 80 percent by weight of the composition will be solid PEG. For example, a liquid polyethylene glycol with molecular weight of 400 (PEG 400) may be blended with a solid polyethylene glycol with a molecular weight of about 2,000 (PEG 2000). The ratio of PEG 400 to PEG 2000 may vary from about 40:60 to about 30:70. These blends may be formed by mixing the liquid PEG and the solid PEG with constant stirring in a heated water bath until the solid melts and a clear liquid solution is formed. After these solutions are allowed to cool and the resulting mixture may be tested for tackiness and used if the desired tackiness is obtained used in the present invention.

Alternatively biocomptaible monosaccharides, disaccharides, polysaccharides or proteins can be used with a biocompatible plasticizer such as glycerine to form tacky films in the presence of water. These materials may be applied to the surface of the buttress material and activated by applying water before contacting with the staple applier.

The amount of releasable adhesive that will be applied depends on a variety of factors such as the releasable adhesive used the desired degree of resistance desired for the foam to release and the geometry of its application. Those skilled in the art will readily be able to determine the appropriate amount of releasable adhesive to apply to achieve the desired release profile.

Additionally, it may be desired for porous foams to be subsequently processed to avoid wicking of the adhesive into the interior of the foam. To prevent or minimize the wicking of the releasable adhesive into the porous foam it is desirable to use seal the surface of the porous foam. There are many methods that can be employed to seal the surface. For example top coating the foam with a low melting biocompatible material before applying the releasable adhesive. Alternatively the porous foam could be top coated with a film layer. Further the porous foam could be treated with a solvent solution to collapse the external layer of pores and form a skin. A similar effect could be achieved by applying a hot surface to the porous foam to substantially reduce the porosity of the surface of the foam.

The aliphatic poly(ester)s are generally prepared by a ring opening polymerization of the desired proportions of one or more lactone monomers in the presence of an organometallic catalyst and an initiator at elevated temperatures. The organometallic catalyst is preferably a tin-based catalyst, e.g. stannous octoate, and is present in the monomer mixture at a molar ratio of monomer to catalyst ranging from about 15,000/1 to about 80,000/1. The initiator is typically an alkanol (such as 1-dodecanol), a polyol (such as 1,2-propanediol, 1,3-propanediol, diethylene glycol, or glycerol, poly(ethylene glycol)s, poly(propylene glycol)s and poly (ethylene-co-propylene glycol)s), a hydroxyacid, or an amine, and is present in the monomer mixture at a molar ratio of monomer to initiator ranging from about 100/1 to about 5000/1. The polymerization is typically carried out at a temperature range from about 80 to about 220° C., preferably 160 to 190° C., until the desired molecular weight and viscosity are achieved.

Figure 4:
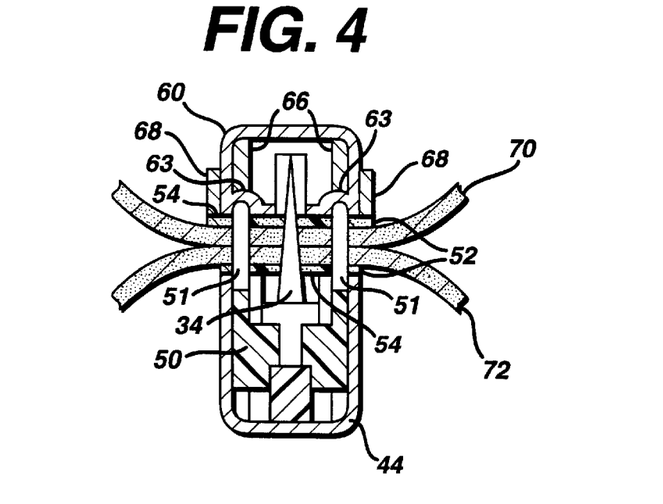
FIG. 4 is a sectional view taken through the jaws of the surgical stapler showing a staple being formed through adjacent tissue sections and foam material positioned adjacent to the outer surface of each of the tissue sections.

The method for achieving hemostasis along a tissue cut having open blood vessels in accordance with the invention will now be discussed along with a discussion of the operation of stapling device 10. The tissue or walls of organ sections to be stapled and cut are positioned and clamped between upper jaw 20 and lower jaw 40 and latch 38 is in its latched position as shown in FIG. 2. At least one, and preferably both, the cartridge 50 and the anvil tip 62 are provided with a strip of foam material 52 as discussed above. For example, as shown in FIG. 4, tissue segments 70 and 72 are shown positioned and clamped between jaws 20 and 40.

After the tissue segments are clamped between the jaw members, stapler 10 is fired by advancing firing knob 42 to activate the pusher block and knife blade assembly 30. The firing wedges 32 advance distally through the staple cartridge 50 into engagement with staple drivers to sequentially drive staples 51 through the openings 53 in two pairs of spaced apart parallel lines of staples. The staples 51 contact a corresponding staple forming pocket associated with anvil section 60 to form generally a B-shaped configuration or a flat configuration staple. Referring to FIG. 4, the formed staples extend through the tissue sections 70 and 72 and the strips of foam material 52. At the same time, knife blade 34 is distally advanced through a longitudinal slot formed in anvil section 60 and staple cartridge 50 to cut the tissue sections gripped between the jaw sections between the two pairs of spaced apart parallel lines of staples.

After the firing wedges 32 are fully advanced to form all of the staples in cartridge 50, the pusher block and knife blade assembly 30 is returned to its start position by retraction of firing knob 42. The latch member 38 may then be moved to its unlatched position, separating jaws 20 and 40, so as to permit the device 10 to be unclamped and removed from the tissue sections releasing the foam material strips from the anvil tip 62 and/or cartridge 50.

Figure 5:
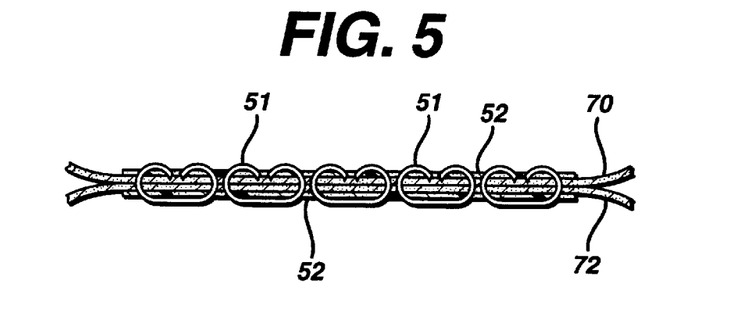
FIG. 5 is a longitudinal sectional view showing adjacent tissue sections joined together by staples and foam material in accordance with the invention.
Figure 6:
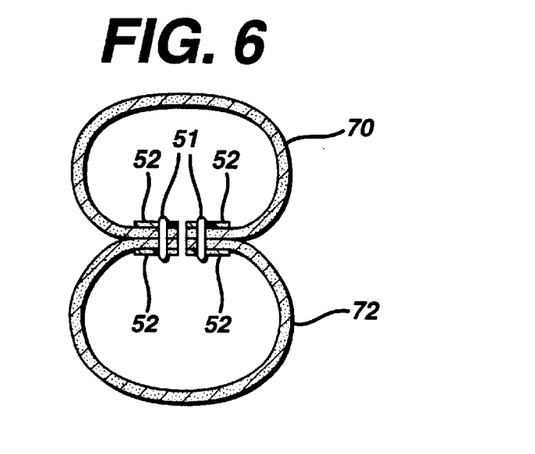
FIG. 6 is a transverse sectional view showing adjacent organ segments joined together by staples and foam material in accordance with the invention.
Figure 7:
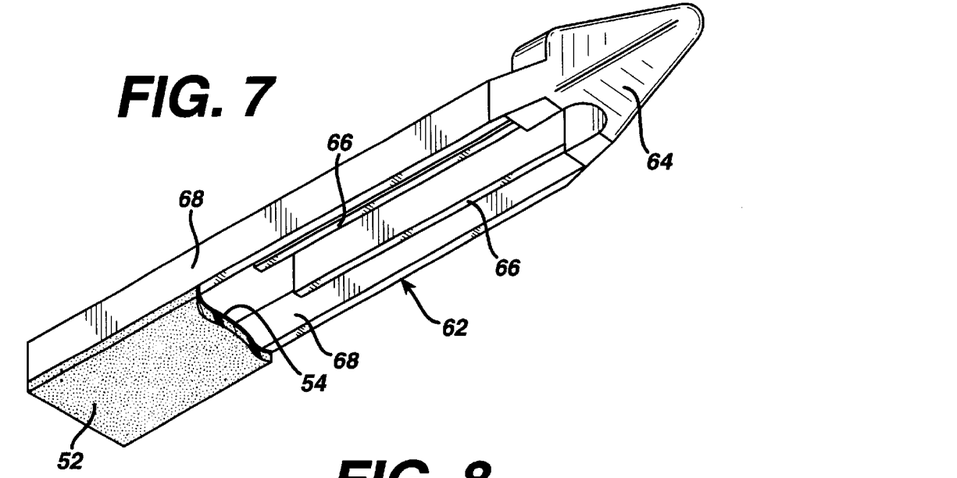
FIG. 7 is a perspective view of an anvil tip that includes a foam material in accordance with the invention.
Figure 8:
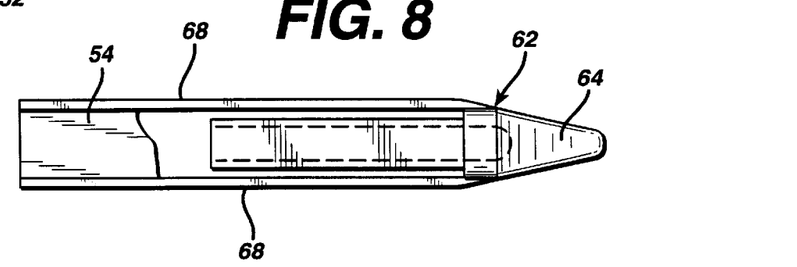
FIG. 8 is a top plan view of the anvil tip shown in FIG. 7.
Figure 9:
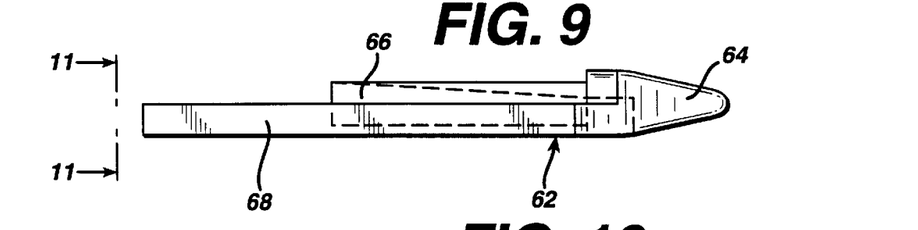
FIG. 9 is a side elevational view of the anvil tip shown in FIG. 7.
Figure 10:
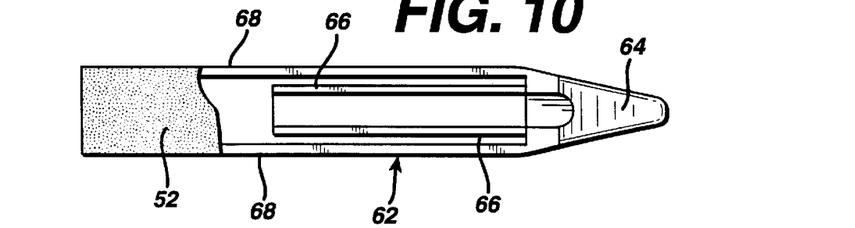
FIG. 10 is a bottom plan view of the anvil tip shown in FIG. 7.
Figure 11:
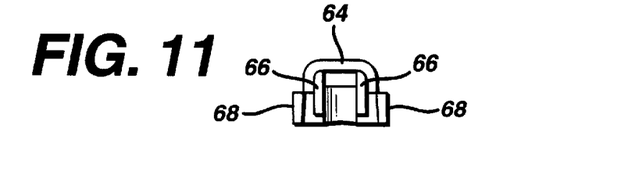
FIG. 11 is an end view of the anvil tip taken along line 11—11 in FIG. 9.

As shown in FIGS. 5 and 6, staples 51 extend through the foam material strips 52 and the tissue segments 70 and 72 sandwiched therebetween. The foam material strips 52 uniformly distribute pressure along the line of staples and thereby cause substantial hemostasis and pneumostasis along the tissue cut and around the staple legs. The absorbable nature of the material from which the foam strips are made allows the strips to be left in the body and eliminates the potential for foreign body reactions that might occur if the foams were not bioabsorbable.

In accordance with the most preferred embodiment of the invention the foam material is positioned adjacent the surfaces of the tissue sections that contact both the staple cartridge 50 and the anvil tip 62. However, the invention contemplates that the foam material may be positioned adjacent only one of such surfaces, preferably the surface adjacent the anvil tip 62. Further, it is preferred that a pair of parallel lines of staples extend through each tissue section adjacent the tissue cut.

Although disclosed above in conjunction with a particular surgical stapler 10 for exemplary purposes, it is contemplated that the principles of the present invention may be similarly utilized in conjunction with other types of surgical staplers and cutters. For example, a circular stapler of the type disclosed in U.S. Pat. No. 5,104,025 may be suitably modified to provide foam material on the staple cartridge and the anvil. An endoscopic linear cutter of the type disclosed in U.S. patent application Ser. No. 779,436, filed Oct. 18, 1991, now abandoned, may be suitably modified to provide foam material on the anvil portion and the staple cartridge assembly.

The method and apparatus of the invention in its broadest aspects is not limited to the specific details shown and described, and modifications may be made to the disclosed; preferred embodiments of the invention without departing from the principles of the invention.

EXAMPLE 1

Synthesis of 50:50 Poly (ε-caprolactone-co-glycolide)for Foam Buttress Material Adhesive 57.07 grams of ε-caprolactone(0.5 mole), 58.04 grams of glycolide (0.5 mole), 5.68 mL (60 mmole/mole) of diethylene glycol, and 67 μL (45K/1 monomer/catalyst ratio) of 0.33M stannous octoate solution in toluene were added to a clean, flame dried, 250 mL single neck round bottom flask in the nitrogen glove box. The contents of the flask were dried overnight under full vacuum at room temperature. After drying overnight the flask was fitted with a flame dried stainless steel mechanical stirrer, vacuum dried for an additional 30 minutes, purged with nitrogen gas, and kept under a nitrogen gas blanket during the polymerization. The flask was placed in an oil bath. The oil bath temperature was raised to 80° C. and was held at 80° C. for ½ hour to completely dissolve the glycolide. The oil temperature was then raised to 190° C. and held for 18 hours. The flask was removed from the oil bath and allowed to cool to room temperature. The copolymer was devolatilized after replacing the mechanical stirrer with a magnetic stirbar for 16 hours at 80° under full vacuum. The finished copolymer was characterized by 1H NMR and inherent viscosity in HFIP (at 25° C. and a concentration of 0.1 g/dL). The NMR results were polygylcolide, 47.3%, polycaprolactone 52.3% residual glycolide monomer less than 0.2%, residual caprolactone monomer less than 0.2%. The IV was 0.19.

EXAMPLE 2

Lyophilization Process for Making Caprolactone Glycolide Foams

This example describes a preferred method for making lyophilized foam from caprolactone-glycolide copolymers.

Making Solution: An appropriate amount (16.5 gm) of polymer (nominal 40/60 CAP/GLY made in a manner similar to the methods described in U.S. Pat. No. 5,468,253) was placed in 1,4-dioxane solvent (148 ml) and stirred at about 50° C. for about 5 hours until dissolved (to make a 10 weight percent solution). The solution was filtered cool through an extra coarse porosity filter (Kimble, Kimax Buchner funnel with Kimflow fritted disc, 150 ml capacity, extra coarse porosity-or equivalent) to remove undissolved polymer.

Lyophilization: An appropriate amount of solution (31.0 g for about a 0.030" thick) was placed in a specially made flat bottom glass dish (constructed from "optically" flat glass bottom and tube) about 8.5" in diameter. The dish was cleaned with caustic and silanized before use. The dish containing the solution was placed on the shelf of the precooled lyophilizer maintained at 20° C. The solution was then allowed to freeze by setting the shelf temperature to −5° C.

After 30 minutes a vacuum was pulled (in one case as long as 1 hour). Two hours of primary drying at −5° C. under vacuum was needed to remove most of the 1,4-dioxane. At the end of this drying phase, typically the vacuum level reaches to about 10 mTorr or less. Next the second phase of the drying was done in two stages under a 10 mTorr vacuum. First the shelf temperature was raised to 5° C. and held for 1 hour, then the temperature was raised to 20° C. and held for an additional 1 hour.

At the end of the second drying phase the chamber was taken to room temperature and the vacuum was broken with nitrogen. The foams are removed from the dishes and placed in plastic bags and stored under nitrogen.

The total cycle time for lyophilization was approximately 4.5 hours. Foams made by this process were determined to have <0.2 ppm of residual dioxane by headspace analysis.

What is claimed is:

1. Apparatus for hemostasis or pneumostasis of tissue comprising
a staple cartridge containing a plurality of surgical staples provided in two spaced apart lines having an upper surface with an opening through which said staples may be ejected, said upper surface having releasably attached thereto a compliant bioabsorbable open cell foam, wherein the open cell foam has at least one surface that has been substantially sealed that is in contact with the upper surface of the cartridge.

2. The apparatus of claim 1 wherein the surface of the open cell foam that has been sealed has been sealed by heating the foam.

3. The apparatus of claim 1 wherein the surface of the open cell foam that has been sealed has been sealed by attaching a biocompatible film to said surface.

4. The apparatus of claim 1 wherein the surface of the open cell foam that has been sealed has been sealed by applying a biocompatible coating to the surface of the foam.

5. The apparatus of claim 1 wherein the surface of the open cell foam that has been sealed has been sealed by contacting the surface of the foam with a solvent.

6. The apparatus of claim 1 wherein the compliant bioabsorbable open cell foam is composed of copolymers of ε-caprolactone and glycolide.

7. The apparatus of claim 1 wherein the compliant bioabsorbable open cell foam is releasably attached to the upper surface of the staple cartridge by a bioabsorbable releasable adhesive.

8. The apparatus of claim 7 wherein the bioabsorbable releasable adhesive is selected from the group consisting of copolymers of ε-caprolactone and trimethylene carbonate, copolymers of ε-caprolactone and an ether lactone, copolymers of trimethylene carbonate and an ether lactone, copolymers composed of in the range of from about 65 mole percent to about 35 mole percent of ε-caprolactone, trimethylene carbonate, ether lactone repeating units or combinations thereof with the remainder of the polymer being a plurality of second lactone repeating units; wherein the second lactone repeating units being selected from the group consisting of glycolide repeating units, lactide repeating units, 1,4-dioxanone repeating units, 6,6-dialkyl-1,4-dioxepan-2-one, combinations thereof and blends thereof.

9. The apparatus of claim 7 wherein the bioabsorbable releasable adhesive is a blend of liquid and low melting polyethylene glycols.

10. The apparatus of claim 7 wherein the bioabsorbable releasable adhesive is a sacccharide and a plasticizer.

11. The apparatus of claim 7 wherein the bioabsorbable releasable adhesive is a protein and a plasticizer.

12. The apparatus of claim 1 wherein the compliant bioabsorbable open cell foam contains an effective amount of a pharmaceutically active compound.

13. The apparatus of claim 7 wherein the releaseable adhesive is a tacky microdispersion.

14. A compliant biocompatible foam having a first side and a second side shaped to fit within the jaws of a staple applier, wherein the compliant bioabsorbable foam is composed of an elastomeric aliphatic polyester and wherein the foam has at least one surface that has been substantially sealed.

15. The compliant biocompatible foam of claim 14 wherein the elastomeric aliphatic polyester is selected from the group consisting of a copolymer of ε-caprolactone and glycolide, a copolymer of ε-caprolactone and lactide (including L-lactide, D-lactide blends thereof or lactic acid) a copolymer of p-dioxanone and lactide (including L-lactide, D-lactide and lactic acid), a copolymer of ε-caprolactone and p-dioxanone, a copolymer of p-dioxanone and trimethylene carbonate, a copolymer of trimethylene carbonate and glycolide, a copolymer of trimethylene carbonate and lactide (including L-lactide, D-lactide, blends thereof or lactic acid) and blends thereof.

16. The compliant biocompatible foam of claim 14, wherein the foam is an open cell foam.

17. The compliant biocompatible foam of claim 16 wherein the compliant biocompatible foam contains an effective amount of a pharmaceutically active compound.

18. The compliant biocompatible foam of claim 14 further comprising on the first side a releasable adhesive selected from the group consisting of copolymers of ε-caprolactone and trimethylene carbonate, copolymers of ε-caprolactone and an ether lactone, copolymers of trimethylene carbonate and an ether lactone, copolymers composed of in the range of from about 65 mole percent to about 35 mole percent of ε-caprolactone, trimethylene carbonate, ether lactone repeating units or combinations thereof with the remainder of the polymer being a plurality of second lactone repeating units; wherein the second lactone repeating units being selected from the group consisting of glycolide repeating units, lactide repeating units, 1,4-dioxanone repeating units, 6,6-dialkyl-1,4-dioxepan-2-one, combinations thereof and blends thereof.

19. The compliant biocompatible foam of claim 14 further comprising a releasable biocompatible adhesive on the first side, wherein the bioabsorbable releasable adhesive comprises a blend of liquid and low melting polyethylene glycols.

20. The compliant biocompatible foam of claim 19 wherein the compliant biocompatible foam contains an effective amount of a pharmaceutically active compound.

21. The compliant biocompatible foam of claim 14 further comprising a releasable biocompatible adhesive on the first side, wherein the bioabsorbable releasable adhesive comprises a saccharide and a plasticizer.

22. The compliant biocompatible foam of claim 21 wherein the compliant biocompatible foam contains an effective amount of a pharmaceutically active compound.

23. The compliant biocompatible foam of claim 14 further comprising a releasable biocompatible adhesive on the first side, wherein the bioabsorbable releasable adhesive comprises a protein and a plasticizer.

24. The compliant biocompatible foam of claim 23 wherein the compliant biocompatible foam contains an effective amount of a pharmaceutically active compound.

25. The compliant biocompatible foam of claim 14 wherein the compliant biocompatible foam contains an effective amount of a pharmaceutically active compound.

26. The compliant biocompatible foam of claim 14 further comprising a releasable biocompatible adhesive on the first sides wherein the releasable adhesive comprises a tacky microdispersion.

27. The compliant biocompatible foam of claim 26 wherein the compliant biocompatible foam contains an effective amount of a pharmaceutically active compound.

28. An apparatus for approximating tissue, comprising; a staple cartridge containing a plurality of surgical staples provided in two spaced apart lines having an upper surface with an opening through which said staples may be ejected, said upper surface having releasably attached thereto a compliant bioabsorbable foam having at least one surface that has been substantially sealed.

29. The apparatus of claim 28, wherein the foam is an open cell foam.

30. The apparatus of claim 28, further comprising a releasable biocompatible adhesive on the first side, wherein the bioabsorbable releasable adhesive comprises a blend of liquid and low melting polyethylene glycols.

31. The apparatus of claim 28, further comprising a releasable biocompatible adhesive on the first side, wherein the bioabsorbable releasable adhesive comprises a saccharide and a plasticizer.

32. The apparatus of claim 28, further comprising a releasable biocompatible adhesive on the first side, wherein the bioabsorbable releasable adhesive comprises a protein and a plasticizer.

33. The apparatus of claim 28, further comprising a releasable biocompatible adhesive on the first side, wherein the releasable adhesive comprises a tacky microdispersion.

* * * * *